United States Patent [19]
Nappholz

[11] Patent Number: 5,800,469
[45] Date of Patent: Sep. 1, 1998

[54] PACEMAKER WITH ANAEROBIC THRESHOLD DETERMINATION

[76] Inventor: Tibor A. Nappholz, 8524 E. Jamison Ave., Englewood, Colo. 80112

[21] Appl. No.: 838,284

[22] Filed: Apr. 16, 1997

[51] Int. Cl.⁶ ............................................. A61N 1/365
[52] U.S. Cl. .................................................... 607/18
[58] Field of Search .................................. 607/17, 18

[56] References Cited

U.S. PATENT DOCUMENTS

| | | | |
|---|---|---|---|
| 4,773,401 | 9/1988 | Citak et al. | 607/17 |
| 4,901,725 | 2/1990 | Nappholz et al. | |
| 5,065,759 | 11/1991 | Beggmann et al. | 607/18 |
| 5,161,527 | 11/1992 | Nappholz et al. | 607/17 |
| 5,292,340 | 3/1994 | Crosby et al. | 607/18 |
| 5,441,523 | 8/1995 | Nappholz | |
| 5,487,753 | 1/1996 | MacCarter et al. | |

*Primary Examiner*—William E. Kamm
*Attorney, Agent, or Firm*—Gottlieb, Rackman & Reisman

[57] ABSTRACT

A rate responsive pacemaker includes a detector for detecting the anaerobic threshold of the patient. The threshold can be logged or can be used to manipulate the pacing regime of the pacemaker. The detector may include two metabolic demand sensors: one which is sensitive to the anaerobic threshold and one that is not. In this manner, the anaerobic threshold can be detected by monitoring the correlation between the two parameters. The parameter sensitive to the anaerobic threshold may be a parameter dependent on the patient's breathing cycle, such as minute volume, while the other parameter is preferably a threshold dependent on the sympathetic control of the body such as the QT interval.

17 Claims, 4 Drawing Sheets

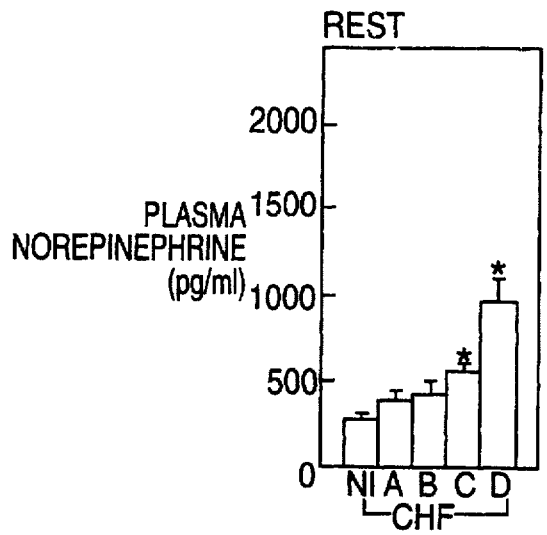
FIG. 2a
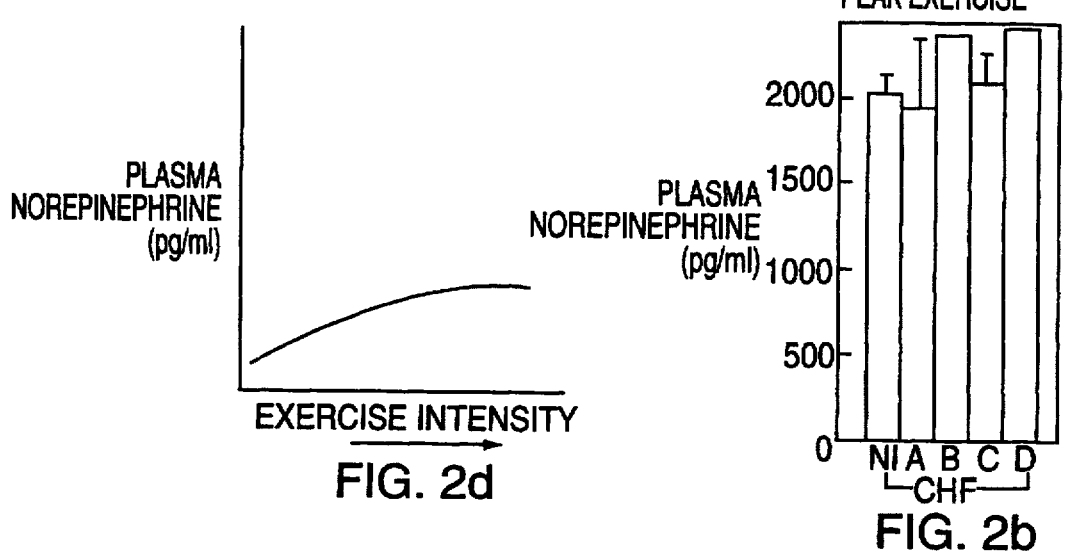
FIG. 2d
FIG. 2b
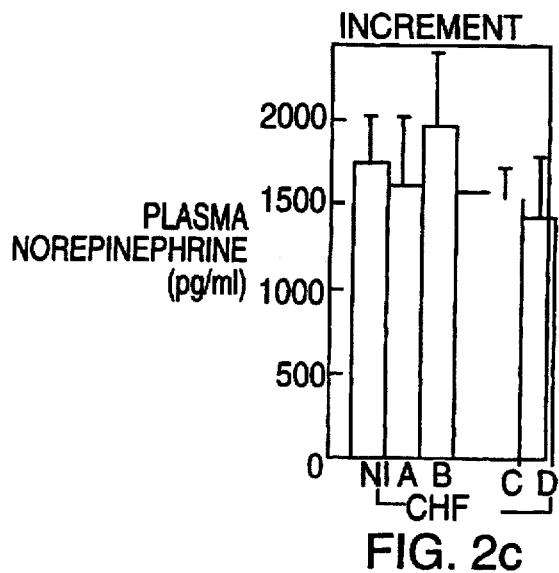
FIG. 2c

PACEMAKER WITH ANAEROBIC THRESHOLD DETERMINATION

BACKGROUND OF THE INVENTION

A. Field of Invention

This invention pertains to a pacemaker or other cardiac stimulation device including means for determining a physiological parameter, such as the anaerobic threshold, which parameter may be used for an optimal cardiac stimulation regime. Two sensors are used to monitor two different hemodynamic parameters, only one which is dependent on the anaerobic threshold. Therefore, if a person's heart is beating above the anaerobic threshold level, the difference between the two sensor outputs can be used as an indication of this threshold level.

B. Description of the Prior Art

The normal automatic cardiac control of a person's body operates so that as a person's need for oxygen intake and $CO_2$ elimination increases gradually, due for example to an extended exercise period, his heart rate is also increased proportionally, thereby increasing the blood flow to compensate for these physiological needs. However, this process cannot go on forever even for very fit persons. Eventually, a point or threshold is reached above which the heart rate cannot be increased any longer. If exercise is continued above this point, the muscles start burning nutrients to generate energy using chemical reactions without oxygen, i.e., anaerobically. Therefore, the point or threshold above which this phenomenon occurs is known as the anaerobic threshold. However, a byproduct of the anaerobic reactions is carbon dioxide which must be expressed from the body in the same manner that carbon dioxide is normally expressed. As a result, during the anaerobic mode, the body must exhale carbon dioxide at a rate greater than during the normal (aerobic mode) leading to an increase in respiration rate, and concurrently, in the minute volume.

The anaerobic threshold varies from one individual to another and it is higher for persons who are physically fit than for persons who are sedentary. Therefore, if a patient's pacemaker is to operate in a hemodynamically optimal mode, its programming should take this threshold in consideration.

In one previous patent it is suggested that in a rate responsive pacemaker using a metabolic demand parameter as an indicia of the patient's physiological demand, a different conformal mapping between the metabolic demand and the corresponding pacing rate be used above and below the threshold level. (See U.S. Pat. No. 5,487,753). However, in this patent, the anaerobic threshold is not determined dynamically for each patient but instead it is assumed that this threshold is at 70% of the patients' peak heart rate. The peak heart rate may be either programmed by the physician, or calculated using the formula:

peak heart rate=220–age (beats per minute).

Therefore, in this patent the physical condition of the patient is ignored.

OBJECTIVES AND SUMMARY OF THE INVENTION

In view of the above, it is an objective of the present invention to provide a pacemaker which automatically detects the anaerobic threshold of a patient.

A further objective is to provide a pacemaker which automatically changes or adjusts its operation to reflect an anaerobic cardiac operation thereby automatically adjusting for changes in the physical condition or fitness of a patient.

Yet, a further objective is to provide a pacemaker which not only measures but logs the anaerobic threshold so that it can be downloaded to a programmer for analysis.

Other objectives and advantages of the invention shall become apparent from the following description. Briefly, a pacemaker constructed in accordance with this invention includes a cardiac sensor for sensing intrinsic cardiac events in one of the heart chambers, a pacing generator for generating cardiac pulses on demand, a first sensor for sensing a first metabolic demand parameter and a second sensor for sensing a second metabolic demand parameter. The two sensors generate corresponding outputs which are normally adjusted so that while the patient is at rest or performing low level exercise, the two outputs track each other. For example, the outputs can be fed into low pass filters having generally long time constants of several days. Importantly, the sensors are selected such that one of the parameters is sensitive to cardiac operations above the anaerobic threshold while the other one is not. Therefore, if the two sensors are continuously or frequently compared, a sudden disparity or lack or correlation between them is indicative of onset for an anaerobic operation.

A controller receives the signal indicative of intrinsic cardiac events as well as the two signals indicative of metabolic demand. The controller generates commands for said pacing generator in one mode below the anaerobic threshold level, and in a different mode when anaerobic operation above the threshold level is indicated.

BRIEF DESCRIPTION OF THE DRAWINGS

FIG. 2a shows the plasma norepinephrine concentration at rest for a normal person as compared to persons having various degrees (A–D) of congestive heart failure;

FIG. 2b shows the plasma norepinephrine concentration at peak exercise for a normal person as compared to persons having various degrees (A–D) of congestive heart failure;

FIG. 2c shows the incremental change in plasma norepinephrine concentration from rest to peak exercise for a normal person as compared to persons having various degrees (A–D) of congestive heart failure;

FIG. 2d shows the variation of plasma norepinephrine with exercise;

DETAILED DESCRIPTION OF THE INVENTION

As previously discussed, a basic principle of the present invention is to use two sensors to monitor metabolic demand: a sensor which monitors a parameter which is sensitive to the anaerobic threshold, and a second sensor which is not. As discussed above, minute volume is a perfect candidate for the first parameter since it is very sensitive to the anaerobic threshold and the operation of the heart at rates exceeding anaerobic threshold.

Figure 1A:
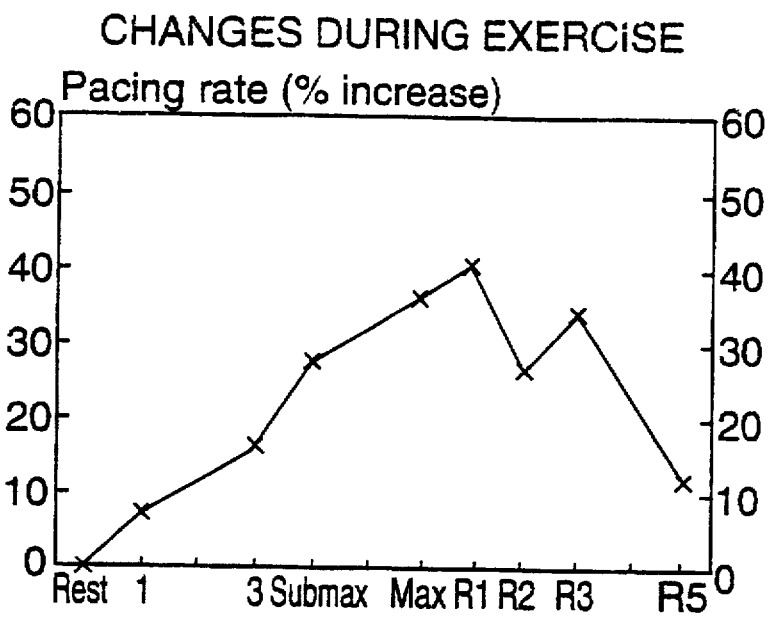
FIGS. 1a and 1b show respectively the increase in pacing rate and noradrenaline concentration in the blood as a function exercise level.
Figure 1B:
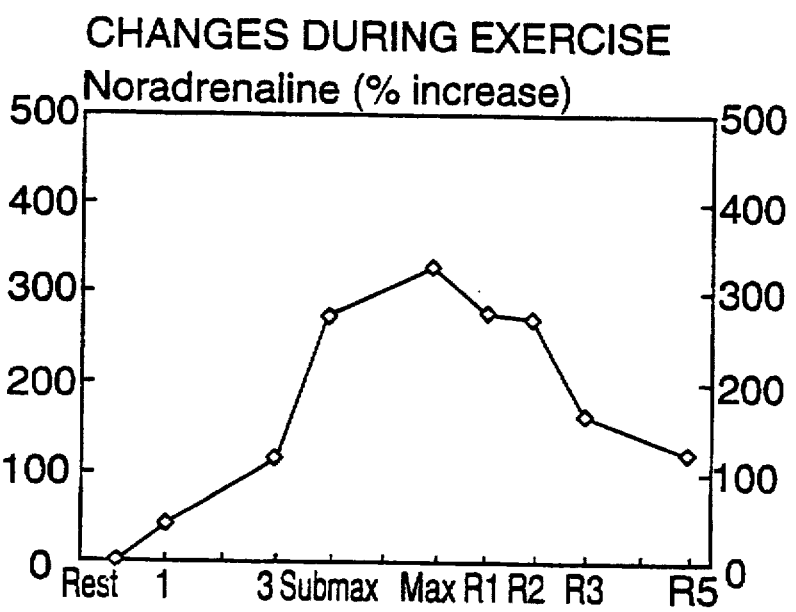

The second sensor should monitor a physiological parameter which is not directly related to $CO_2$. Two such parameters are the QT interval and the presence or concentration of Noradrenaline(TM)—a major neural stimulant. There are many studies relating pacing rate to QT and the relationships to heart rates to noradrenaline are well known, and hence the later is used to show that QT is a parameter of interest for this application. FIGS. 1a and 1b show the relations of the increase in pacing rate and the increase noradrenaline respectively. This comparison shows that the generation of the sympathetic stimulation is in direct response to metabolic demand and is meditated by the central nervous system. In these Figures R1 . . . R5 refer to consecutive rest periods.

FIGS. 2a–2d show that independent of patient condition the increase of norepinephrine is similar for all patients from rest to maximum exertion. FIG. 2d further indicates that appreciably at higher levels of exertion, the increase in norepinephrine levels off slightly.

Consequently, QT which is related to norepinephrine (sympathetic enervation) is a good parameter to track MV with, as it will clearly depart from MV at the anncarobic threshold.

Figure 3:
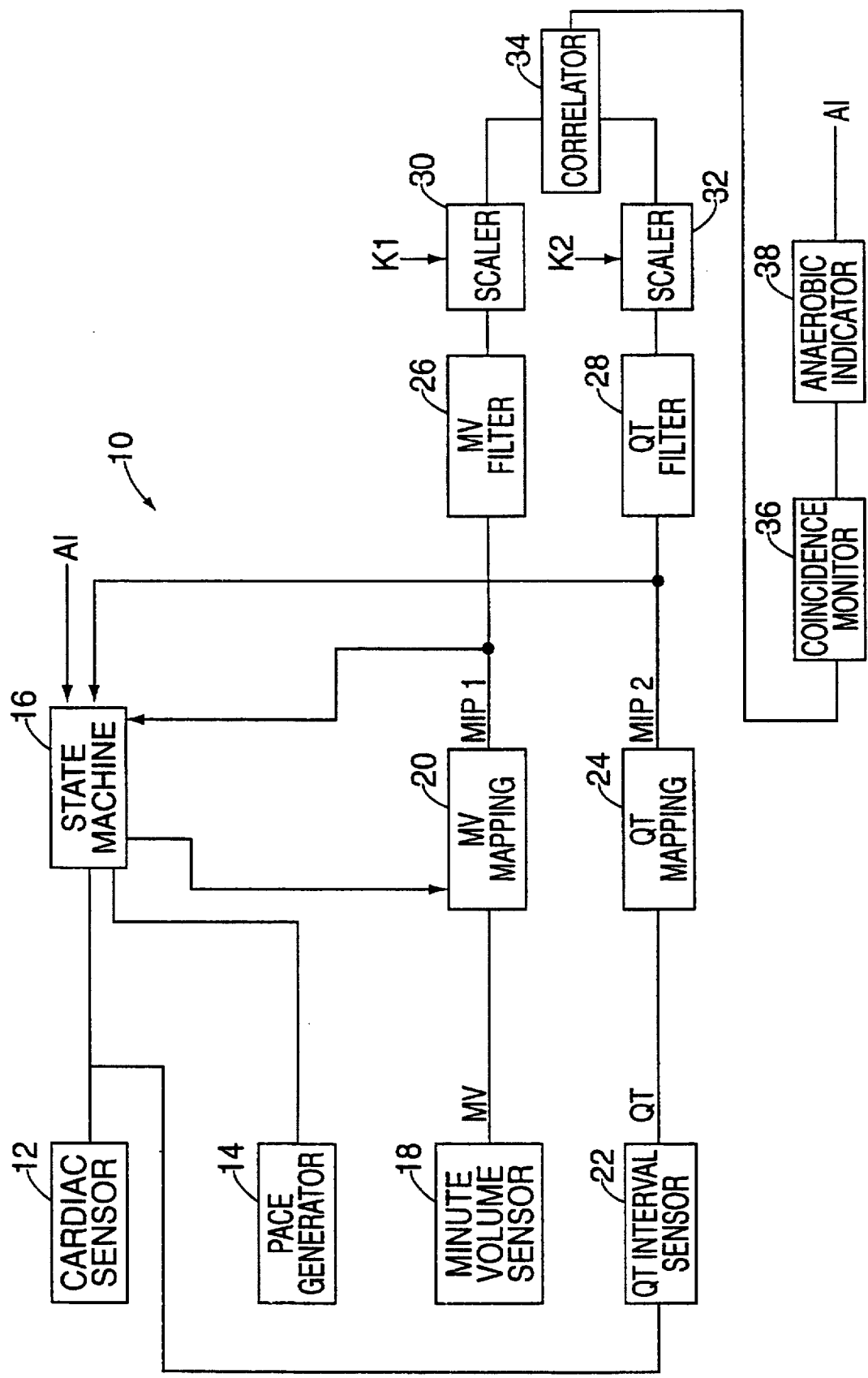
FIG. 3 shows a block diagram for a pacemaker constructed in accordance with this invention.

A block diagram of a pacemaker with two metabolic demand sensors for sensing the anaerobic threshold in FIG. 3. In this Figure, a pacemaker 10 includes a cardiac sensor 12 for sensing intrinsic cardiac events. A pulse generator 14 is also provided to generate pacing pulses on demand in response to commands from a state machine 16. (Depending on the mode of operation of the pacemaker 10, the sensor may be used to sense electrical activity in the right atrium, right ventricle, or both, however, a single chamber sensing and pacing is described for the sake of simplicity.)

The pacemaker is further provided with two metabolic sensors for sensing the metabolic demand of the patient. The first sensor is a minute volume sensor 18. An example of such sensor is described in U.S. Pat. No. 4,901,725. Briefly, the sensor measures the transthoracic impedance across the chest cavity of the patient during at least one breathing cycle. This impedance is related to the minute volume parameter (MV). This parameter is fed to an MV mapping circuit 20 for mapping the MV into a corresponding metabolic indicated parameter (MIP1) which may be, for example, a pacing rate. The parameter MIP1 is then fed to the state machine 16. The state machine 16 analyzes the cardiac events sensed by sensor 12, and based on a set of programmed rules, it generates pacing commands on demand to pace generator 14. A state machine of this kind is described in U.S. Pat. No. 5,441,523 incorporated herein by reference.

In addition, a second sensor 22 is also provided for measuring the QT interval, for example, from the events sensed by sensor 12. The sensor 22 thus provides a metabolic demand parameter QT. This parameter is fed to a QT mapping circuit which generates a second metabolic indicated parameter MIP2. A QT interval sensor is disclosed in U.S. Pat. No. 4,624,954.

The two metabolic indicated parameters MIP1 and MIP2 are fed to respective low pass filters 26 and 28 which have a very long time constant, in terms of 30 days or so. These filters, in effect, then generate weighed average values for these parameters. Since by far the most prevalent physical activity for all persons is rest, this weighed average is effectively the rest value for these parameters. The two averaged values are fed to two scaler circuits 30, 32 where they are scaled by scaling constants k1 and k2 selected so that the two averaged parameters have the same value. Finally, the two scaled averaged parameters are fed to a correlator 34. The correlator 34 correlates these two averaged values and generates an output which is monitored by a coincidence monitor 36. The output of the monitor 36 is fed to an indicator 38 which generates an output AI (anaerobic threshold indication) when the monitor detects that there is an excessive disparity indicated by the correlator 34. This disparity may be quantitatively determined either as a difference, a ratio, or by more sophisticated correlation calculations.

Figure 4:
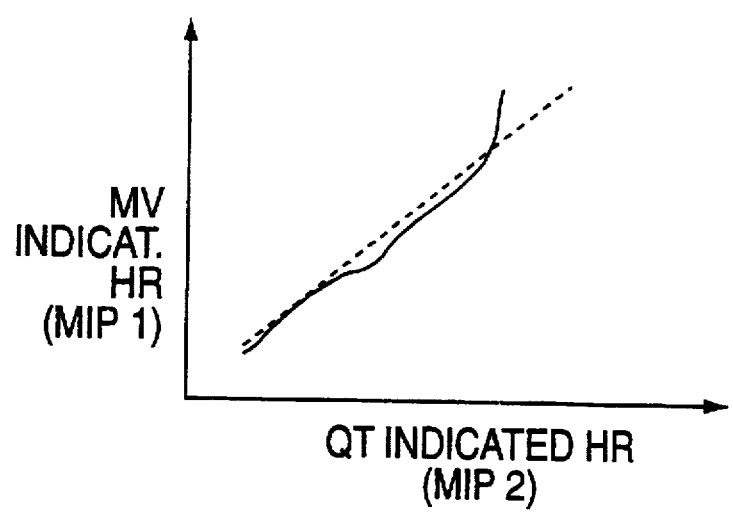
FIG. 4 shows a graph correlating the minute volume indicated rate with the QT indicated rate.

The circuit operates as follows. As long as the heart operates below the anaerobic threshold, the two metabolic parameters MIP1 and MIP2 track each other, as shown in FIG. 4. Their average value as indicated by the filters 26, 28 also track each other and hence the correlator 34 indicates a good correlation between these parameters.

As seen in FIG. 4, when the anaerobic threshold is exceeded, however, the MIP1 due to the minute volume starts to deviate significantly from the second parameter MIP2. This deviation will propagate through to the correlator 34 and as a result, when a sufficiently large loss of correlation is detected by monitor 36, this monitor 36 triggers the indicator 38 thereby activation the signal AI.

Signal AI is an important signal because it flags the exercise level at which the heart has reached its limits to provide the body with sufficient oxygen. In essence, it provides a means for monitoring the cardiac output. In patients with impaired cardiac function, this threshold may be exceeded several times a day, even if the patient is involved only in light exercise. Therefore, the pacemaker makes use of this parameter to adjust its operation, preferably in a manner so as to minimize the number of times the anaerobic threshold is exceeded. For example, as previously mentioned, the threshold may be used by the MV mapping circuit 20 to generate MIP1. This parameter is in turn used by the state machine 16 to generate pacing commands, as described in U.S. Pat. No. 5,487,753, with the anaerobic threshold being indicated by AI.

Alternatively, while AI is active, the state machine 16 may use MIP2 rather than MIP1 as the metabolic demand parameter. Finally, a memory 40 may be used to store each incidence when AI occurs together with a corresponding value for MIP1. This information is downloaded into a programmer later for analysis.

It should be understood that the QT interval used as the second metabolic indicated parameter is driven by sympathetic contractility drive which is the primary driver for contractibility.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims used to modify the RRF function for converting a metabolic indicated demand to a pacing parameter. In this manner, the pacemaker operation is optimized by adjusting its operation automatically to conform to the actual anaerobic threshold level of the patient.

I claim:

1. An implantable pacemaker comprising:
    an intrinsic event sensor for sensing intrinsic cardiac events, said sensor generating a sensed signal;
    a pace generator for generating pacing signals in response to first and second commands;
    an anaerobic threshold detector for generating an anaerobic indication corresponding to an anaerobic threshold of the patient; and a controller receiving said sensed signal and said anaerobic indication, and generating in response said first and second commands, said first and second commands defining respective first and a second modes of operation, said first commands being generated by said controller when said anaerobic indication is indicative of a normal condition of said patient and said second commands being generated by said controller when said anaerobic indication is indicative of an anaerobic condition of said patient.

2. The pacemaker of claim 1 further comprising a metabolic demand detector for detecting a metabolic demand of the patient, said metabolic demand sensor generating a metabolic demand signal, said controller receiving said metabolic demand signal for generating said commands.

3. The pacemaker of claim 1 wherein said metabolic demand detector includes a first sensor for sensing a first metabolic parameter and a second sensor for generating a second demand parameter, wherein said first demand parameter is dependent on said anaerobic threshold and wherein said second demand parameter is independent of said anaerobic threshold, said anaerobic indicator including a comparator for comparing said first and second demand parameters to detect said anaerobic threshold.

4. An implantable rate responsive pacemaker comprising:
   a cardiac sensor for sensing intrinsic cardiac activity of a patient and for generating in response a sensed signal;
   a first metabolic demand sensor for sensing a first metabolic demand, said first metabolic demand being sensitive to an anaerobic threshold;
   a second metabolic demand sensor for sensing a second metabolic parameter, said second metabolic parameter being substantially insensitive to said anaerobic threshold;
   an anaerobic threshold detector for generating an anaerobic threshold indication from said first and second metabolic demand parameters;
   a pacing generator for generating pacing pulses in response to commands; and
   a controller for generating said commands in response to said sensed signal, at least one of said metabolic demand parameters and said anaerobic threshold indication.

5. The pacemaker of claim 4 wherein one of said first and second metabolic demand sensors is arranged and constructed to sense a metabolic parameter related to the breathing of said patient.

6. The pacemaker of claim 5 wherein said one metabolic demand sensor is arranged and constructed to sense a minute volume.

7. The pacemaker of claim 5 wherein the other of said first and second metabolic parameter sensors is constructed and arranged to sense a QT interval.

8. The pacemaker of claim 4 further comprising a mapping circuit for mapping one of said metabolic parameters into a corresponding metabolic indicated pacing parameter, said metabolic indicated parameter being received by said controller to generate said commands.

9. The pacemaker of claim 8 wherein said mapping circuit is arranged and constructed to receive said anaerobic threshold indication and to generates said metabolic indicated pacing parameter in accordance with said anaerobic threshold as indicated by said threshold indication.

10. The pacemaker of claim 4 wherein said anaerobic threshold detector includes a correlator for correlating said metabolic demand parameters to generate a correlated output and a correlation analyzer arranged to receive said correlator output to determine a lack of correlation between said parameters, said anaerobic threshold detector generating said anaerobic threshold indication to indicate said anaerobic threshold in the presence of said lack of correlation.

11. The pacemaker of claim 10 wherein said anaerobic threshold detector further include a long term filter for averaging said metabolic indicated parameters.

12. The pacemaker of claim 11 wherein said filter filters said parameters before feeding to said correlator.

13. The pacemaker of claim 4 wherein one of said metabolic indicated parameter sensors is arranged and constructed to sense a parameter which is dependent on a sympathetic enervation of the cardiovascular system.

14. The pacemaker of claim 13 wherein said one parameter is a QT interval.

15. The pacemaker of claim 13 wherein said one parameter is dependent on the cardiac contractility.

16. The pacemaker of claim 4 further comprising a memory for recording a condition of the patient, said condition being dependent in said anaerobic threshold.

17. The pacemaker of claim 4 wherein said controller generates first and second commands, said first and second commands defining respectively a first and a second mode of operation, said first commands being generated when said anaerobic threshold indication is indicative of an anaerobic condition and said second commands being generated when said anaerobic threshold is indicative of an absence of said anaerobic condition.

* * * * *